(12) United States Patent
Kobayashi et al.

(10) Patent No.: US 9,353,350 B2
(45) Date of Patent: May 31, 2016

(54) METHOD FOR PRODUCING MULTIPOLAR CELL

(71) Applicant: TOAGOSEI CO., LTD., Tokyo (JP)

(72) Inventors: Nahoko Kobayashi, Tsukuba (JP);
Tetsuhiko Yoshida, Tsukuba (JP); Yuki Kobayashi, Fujisawa (JP)

(73) Assignee: TOAGOSEI CO. LTD., Tokyo (JP)

( * ) Notice: Subject to any disclaimer, the term of this patent is extended or adjusted under 35 U.S.C. 154(b) by 0 days.

(21) Appl. No.: 14/366,971

(22) PCT Filed: Dec. 20, 2012

(86) PCT No.: PCT/JP2012/083110
§ 371 (c)(1),
(2) Date: Jun. 19, 2014

(87) PCT Pub. No.: WO2013/094698
PCT Pub. Date: Jun. 27, 2013

(65) Prior Publication Data
US 2015/0004697 A1 Jan. 1, 2015

(30) Foreign Application Priority Data
Dec. 20, 2011 (JP) ................................ 2011-278975

(51) Int. Cl.
| | | |
|---|---|---|
| C12N 5/00 | (2006.01) |
| C12N 5/02 | (2006.01) |
| A61K 38/08 | (2006.01) |
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| C12N 5/09 | (2010.01) |
| A61K 35/13 | (2015.01) |
| A61K 35/12 | (2015.01) |
| C07K 7/06 | (2006.01) |

(52) U.S. Cl.
CPC .............. *C12N 5/0693* (2013.01); *A61K 35/12* (2013.01); *A61K 35/13* (2013.01); *C07K 7/06* (2013.01); *C12N 2501/998* (2013.01); *C12N 2503/02* (2013.01)

(58) Field of Classification Search
None
See application file for complete search history.

(56) References Cited

U.S. PATENT DOCUMENTS

| 5,595,756 | A | 1/1997 | Bally et al. |
| 6,344,443 | B1 | 2/2002 | Liu et al. |
| 2007/0021347 | A1 | 1/2007 | Khan et al. |
| 2010/0297758 | A1 | 11/2010 | Yoshida et al. |
| 2012/0122225 | A1 | 5/2012 | Kobayashi et al. |
| 2012/0149053 | A1 | 6/2012 | Yoshida et al. |
| 2013/0323776 | A1 | 12/2013 | Yoshida et al. |
| 2015/0018286 | A1* | 1/2015 | Kobayashi et al. ......... 514/19.3 |

FOREIGN PATENT DOCUMENTS

| CN | 1763082 A | 4/2006 |
| DE | 102009021681 A1 | 11/2010 |
| WO | 03024408 A2 | 3/2003 |
| WO | 03037172 A2 | 5/2003 |
| WO | 2004005472 A2 | 1/2004 |
| WO | 2004/020457 A2 | 3/2004 |
| WO | 2007/004869 A2 | 1/2007 |
| WO | 2007056188 A1 | 5/2007 |
| WO | 2008/081812 A1 | 7/2008 |
| WO | WO 2009/093692 A1 | 7/2009 |
| WO | WO 2011/013698 A1 | 2/2011 |
| WO | WO 2011/013699 A1 | 2/2011 |

OTHER PUBLICATIONS

Paradis-Bleau et al., "Peptide inhibitors of the essential cell division protein FtsA", *Protein Engineering, Design & Selection*, 2005, pp. 85-91, vol. 18, No. 2, Oxford University Press.
Paradis-Bleau et al., "Identification of *Pseudomonas aeruginosa* FtsZ peptide inhibitors as a tool for development of novel antimicrobials", *Journal of Antimicrobial Chemotherapy*, Jun. 2004, pp. 278-280.
Cho et al., "Depletion of CPAP by RNAi disrupts centrosome integrity and induces multipolar spindles", *Biochemical and Biophysical Research Communications*, 2006, pp. 742-747, vol. 339.
Sakaushi et al., "Live imaging of spindle pole disorganization in docetaxel-treated multicolor cells", *Biochemical and Biophysical Research Communications*, 2007, pp. 655-660, vol. 357.
Jaiswal et al., "9-Bromonoscapine-induced mitotic arrest of cigarette smoke condensate-transformed breast epithelial cells", *J Cell Biochem.*, Apr. 15, 2009, pp. 1-20, vol. 106, No. 6.
International Search Report issued in International Patent Application No. PCT/JP2012/083110 mailed Jan. 29, 2013.
Vollmer, "The prokaryotic cytoskeleton: a putative target for inhibitors and antibiotics?," Applied Microbiology and Biotechnology, vol. 73, pp. 37-47, 2006.
Huang et al., "Targeting FtsZ for anti-tuberculosis drug discovery: non-cytotoxic taxanes as novel anti-tuberculosis agents," J. Med Chem, vol. 49, No. 2, pp. 463-466, Jan. 26, 2006.

(Continued)

*Primary Examiner* — James H Alstrum Acevedo
*Assistant Examiner* — Thea D'Ambrosio
(74) *Attorney, Agent, or Firm* — Oliff PLC

(57) ABSTRACT

This invention provides a multipolar cell including three or more centrosomes dispersed therein and a multipolar spindle formed so as to extend from the three or more respective centrosomes. The multipolar cell production method provided by the present invention supplies cultured eukaryotic cells with a synthetic peptide as a multipolarity-inducing peptide, with the synthetic peptide having an amino acid sequence selected from SEQ ID NO: 1 to SEQ ID NO: 12 or an amino acid sequence formed by substituting, deleting and/or adding one, two or three amino acid residues in/from/to the selected amino acid sequence.

8 Claims, 5 Drawing Sheets

(56) References Cited

OTHER PUBLICATIONS

Jul. 3, 2014 International Preliminary Report on Patentability issued in International Patent Application No. PCT/ JP2012/083109.
May 29, 2015 Extended European Search Report issued in European Patent Application No. 12860097.0.
Läppchen et al., "Probing FtsZ and Tubulin with C8-Substituted GTP Analogs Reveals Differences in Their Nucleotide Binding Sites," Chemistry & Biology, vol. 15, pp. 189-199, Feb. 2008.
Ojima et al., "Drug discovery targeting cell division proteins, microtubules and FtsZ," Bioorganic & Medicinal Chemistry, vol. 22, pp. 5060-5077, Mar. 5, 2014.
Jul. 28, 2015 Office Action issued in U.S. Appl. No. 14/267,204.
Sporn et al., "Chemoprevention of cancer," Carcinogensis, vol. 21, No. 3, pp. 525-530, 2000.
Ito et al., "Co-culture of human breast adenocarcinoma MCF-7 cells and human dermal fibroblasts enhances the production of matrix metalloproteinases 1, 2 and 3 in fibroblasts," British Journal of Cancer, vol. 71, pp. 1039-1045, 1995.
Raderschall et al., "Elevated Levels of Rad51 Recombination Protein in Tumor Cells," Cancer Research, vol. 62, pp. 219-225, Jan. 1, 2002.
Neidle, "Cancer Drug Design and Discovery," Elsevier/Academic Press, pp. 427-431, 2008.
Chabner et al., "Cellular and Molecular Basis of Cancer," Merck Manual Professional, pp. 1-5, last accessed May 10, 2012.
J. Rudinger, "Peptide Hormones," University Park Press, pp. 1-7, 1976.
SIGMA, "Custom Peptide Synthesis," pp. 1-2, 2004.
Berendsen, "A Glimpse of the Holy Grail?," Science, vol. 282, pp. 642-643, Oct. 23, 1998.
Voet et al., "Biochemistry," John Wiley & Sons Inc., pp. 235-241, 1995.
Ngo et al., "Computational Complexity Protein Structure Prediction, and the Levinthal Paradox," pp. 491-494, 1994.
Bradley et al., "Limits of Cooperativity in a Structurally Modular Protein: Response of the Notch Ankyrin Domain to Analogous Alanine Substitutions in Each Repeat," Journal of Microbiology, vol. 324, pp. 373-386, 2002.
Jul. 3, 2014 International Preliminary Report on Patentability issued in International Patent Application No. PCT/ JP2012/083111.
Jun. 23, 2015 Office Action issued in U.S. Appl. No. 14/367,023.
U.S. Appl. No. 14/367,023, filed Jun. 19, 2014 in the name of Nahoko Kobayashi.
U.S. Appl. No. 14/367,204, filed Jun. 19, 2014 in the name of Nahoko Kobayshi.
Mar. 12, 2013 International Search Report issued in International Patent Application No. PCT/JP2012/083109.
Jan. 29, 2013 International Search Report issued in International Patent Application No. PCT/JP2012/083111.

* cited by examiner

SEQUENCE LISTING

<160> NUMBER OF SEQ ID NOS: 32

<210> SEQ ID NO 1
<211> LENGTH: 9

-continued

```
<212> TYPE: PRT
<213> ORGANISM: Artificial Sequence
<220> FEATURE:
<223> OTHER INFORMATION: Synthetic peptide

<400> SEQUENCE: 1

Cys Ser Ser Ala Thr Gly Lys Ser Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Cys Leu Ala Pro Ser Pro Ser Lys Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Cys Leu Gly Gln Thr Lys Met Arg Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Cys Gly His Arg Pro Tyr Gln Tyr Cys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Cys Trp Ala Phe Pro Leu His His Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Cys Thr Leu Asn Ser His Ser Asn Cys
1               5

<210> SEQ ID NO 7
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 7

Cys Glu Ile Ser Ala Lys Arg Thr Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Cys His Ile Leu His Ala Gln Ala Cys
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Cys Pro Arg Pro Pro Ser Leu Glu Cys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Cys Thr Gly His Trp Ala Ser Glu Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Cys Ser Tyr Glu Lys Arg Pro Met Cys
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Cys Leu Thr Lys Ser Tyr Thr Ser Cys
1               5

<210> SEQ ID NO 13
<211> LENGTH: 13
<212> TYPE: PRT
<213> ORGANISM: Homo sapiens
```

```
<220> FEATURE:

<400> SEQUENCE: 13

Lys Lys Arg Thr Leu Arg Lys Asn Asp Arg Lys Lys Arg
1               5                   10

<210> SEQ ID NO 14
<211> LENGTH: 8
<212> TYPE: PRT
<213> ORGANISM: Avian infectious bronchitis virus
<220> FEATURE:

<400> SEQUENCE: 14

Trp Arg Arg Gln Ala Arg Phe Lys
1               5

<210> SEQ ID NO 15
<211> LENGTH: 14
<212> TYPE: PRT
<213> ORGANISM: Homo sapiens
<220> FEATURE:

<400> SEQUENCE: 15

Arg Ser Arg Lys Tyr Thr Ser Trp Tyr Val Ala Leu Lys Arg
1               5                   10

<210> SEQ ID NO 16
<211> LENGTH: 19
<212> TYPE: PRT
<213> ORGANISM: Homo sapiens
<220> FEATURE:

<400> SEQUENCE: 16

Met Ala Lys Ser Ile Arg Ser Lys His Arg Gln Met Arg Met Met
1               5                   10                  15

Lys Arg Glu

<210> SEQ ID NO 17
<211> LENGTH: 16
<212> TYPE: PRT
<213> ORGANISM: herpes simplex virus 1
<220> FEATURE:

<400> SEQUENCE: 17

Met Ala Arg Arg Arg Arg His Arg Gly Pro Arg Arg Pro Arg Pro Pro
1               5                   10                  15

<210> SEQ ID NO 18
<211> LENGTH: 19
<212> TYPE: PRT
<213> ORGANISM: Homo sapiens
<220> FEATURE:

<400> SEQUENCE: 18

Gly Arg Cys Arg Arg Leu Ala Asn Phe Gly Pro Arg Lys Arg Arg
1               5                   10                  15

Arg Arg Arg

<210> SEQ ID NO 19
<211> LENGTH: 16
<212> TYPE: PRT
<213> ORGANISM: Marek's disease gammaherpesvirus MKT-1
<220> FEATURE:

<400> SEQUENCE: 19
```

```
Arg Arg Arg Lys Arg Asn Arg Asp Ala Arg Arg Arg Arg Lys Gln
1               5                   10                  15

<210> SEQ ID NO 20
<211> LENGTH: 17
<212> TYPE: PRT
<213> ORGANISM: Homo sapiens
<220> FEATURE:

<400> SEQUENCE: 20

Met Gln Arg Lys Pro Thr Ile Arg Arg Lys Asn Leu Arg Leu Arg Arg
1               5                   10                  15

Lys

<210> SEQ ID NO 21
<211> LENGTH: 22
<212> TYPE: PRT
<213> ORGANISM: Artificial Sequence
<220> FEATURE:
<223> OTHER INFORMATION: Synthetic peptide

<400> SEQUENCE: 21

Cys Ser Ser Ala Thr Gly Lys Ser Cys Lys Lys Arg Thr Leu Arg Lys
1               5                   10                  15

Asn Asp Arg Lys Lys Arg
            20

<210> SEQ ID NO 22
<211> LENGTH: 22
<212> TYPE: PRT
<213> ORGANISM: Artificial Sequence
<220> FEATURE:
<223> OTHER INFORMATION: Synthetic peptide

<400> SEQUENCE: 22

Cys Leu Ala Pro Ser Pro Ser Lys Cys Lys Lys Arg Thr Leu Arg Lys
1               5                   10                  15

Asn Asp Arg Lys Lys Arg
            20

<210> SEQ ID NO 23
<211> LENGTH: 22
<212> TYPE: PRT
<213> ORGANISM: Artificial Sequence
<220> FEATURE:
<223> OTHER INFORMATION: Synthetic peptide

<400> SEQUENCE: 23

Cys Leu Gly Gln Thr Lys Met Arg Cys Lys Lys Arg Thr Leu Arg Lys
1               5                   10                  15

Asn Asp Arg Lys Lys Arg
            20

<210> SEQ ID NO 24
<211> LENGTH: 22
<212> TYPE: PRT
<213> ORGANISM: Artificial Sequence
<220> FEATURE:
<223> OTHER INFORMATION: Synthetic peptide

<400> SEQUENCE: 24

Cys Gly His Arg Pro Tyr Gln Tyr Cys Lys Lys Arg Thr Leu Arg Lys
1               5                   10                  15
```

Asn Asp Arg Lys Lys Arg
            20

<210> SEQ ID NO 25
<211> LENGTH: 22
<212> TYPE: PRT
<213> ORGANISM: Artificial Sequence
<220> FEATURE:
<223> OTHER INFORMATION: Synthetic peptide

<400> SEQUENCE: 25

Cys Trp Ala Phe Pro Leu His His Cys Lys Lys Arg Thr Leu Arg Lys
1               5                   10                  15

Asn Asp Arg Lys Lys Arg
            20

<210> SEQ ID NO 26
<211> LENGTH: 22
<212> TYPE: PRT
<213> ORGANISM: Artificial Sequence
<220> FEATURE:
<223> OTHER INFORMATION: Synthetic peptide

<400> SEQUENCE: 26

Cys Thr Leu Asn Ser His Ser Asn Cys Lys Lys Arg Thr Leu Arg Lys
1               5                   10                  15

Asn Asp Arg Lys Lys Arg
            20

<210> SEQ ID NO 27
<211> LENGTH: 22
<212> TYPE: PRT
<213> ORGANISM: Artificial Sequence
<220> FEATURE:
<223> OTHER INFORMATION: Synthetic peptide

<400> SEQUENCE: 27

Cys Glu Ile Ser Ala Lys Arg Thr Cys Lys Lys Arg Thr Leu Arg Lys
1               5                   10                  15

Asn Asp Arg Lys Lys Arg
            20

<210> SEQ ID NO 28
<211> LENGTH: 22
<212> TYPE: PRT
<213> ORGANISM: Artificial Sequence
<220> FEATURE:
<223> OTHER INFORMATION: Synthetic peptide

<400> SEQUENCE: 28

Cys His Ile Leu His Ala Gln Ala Cys Lys Lys Arg Thr Leu Arg Lys
1               5                   10                  15

Asn Asp Arg Lys Lys Arg
            20

<210> SEQ ID NO 29
<211> LENGTH: 22
<212> TYPE: PRT
<213> ORGANISM: Artificial Sequence
<220> FEATURE:
<223> OTHER INFORMATION: Synthetic peptide

<400> SEQUENCE: 29

Cys Pro Arg Pro Pro Ser Leu Glu Cys Lys Lys Arg Thr Leu Arg Lys
1               5                   10                  15

```
Asn Asp Arg Lys Lys Arg
            20

<210> SEQ ID NO 30
<211> LENGTH: 22
<212> TYPE: PRT
<213> ORGANISM: Artificial Sequence
<220> FEATURE:
<223> OTHER INFORMATION: Synthetic peptide

<400> SEQUENCE: 30

Cys Thr Gly His Trp Ala Ser Glu Cys Lys Lys Arg Thr Leu Arg Lys
1               5                   10                  15

Asn Asp Arg Lys Lys Arg
            20

<210> SEQ ID NO 31
<211> LENGTH: 22
<212> TYPE: PRT
<213> ORGANISM: Artificial Sequence
<220> FEATURE:
<223> OTHER INFORMATION: Synthetic peptide

<400> SEQUENCE: 31

Cys Ser Tyr Glu Lys Arg Pro Met Cys Lys Lys Arg Thr Leu Arg Lys
1               5                   10                  15

Asn Asp Arg Lys Lys Arg
            20

<210> SEQ ID NO 32
<211> LENGTH: 22
<212> TYPE: PRT
<213> ORGANISM: Artificial Sequence
<220> FEATURE:
<223> OTHER INFORMATION: Synthetic peptide

<400> SEQUENCE: 32

Cys Leu Thr Lys Ser Tyr Thr Ser Cys Lys Lys Arg Thr Leu Arg Lys
1               5                   10                  15

Asn Asp Arg Lys Lys Arg
            20
```

METHOD FOR PRODUCING MULTIPOLAR CELL

TECHNICAL FIELD

The present invention relates to a synthetic peptide for inducing multipolarity in target cells. In particular, it relates to a method for producing a cell with extra centrosomes, that is, a multipolar cell, by supplying the peptide to the target cells.

The present application claims priority based on Japanese Patent Application No. 2011-278975 filed on Dec. 20, 2011 and its entire content is incorporated herein by reference. The present application is a National Stage application of PCT Application No. PCT/JP2012/083110 filed on Dec. 20, 2012.

BACKGROUND ART

One of the characteristics of tumor cells (cancer cells) is that as compared to normal cells, they undergo rapid cell division, resulting in a significantly high cell proliferation rate. Thus, as anticancer agents to kill tumor cells or to inhibit their proliferation, drugs that inhibit division of tumor cells (cancer cells) are used. For example, alkylating agents are drugs that act on the DNA of tumor cells (cancer cells) to crosslink the bases between double strands, thereby inhibiting DNA replication and blocking cell division. Antimetabolites such as 5-FU, etc., are drugs that inhibit DNA synthesis and block cell division.

CITATION LIST

Patent Literature

[Patent Document 1] WO 2009/093692A
[Patent Document 2] WO 2011/013698A
[Patent Document 3] WO 2011/013699A

Non-Patent Literature

[Non-Patent Document 1] Protein Engineering, Design & Selection, vol. 18(2), 2005, pp. 85-91
[Non-Patent Document 2] Journal of Antimicrobial Chemotherapy, vol. 54(1), 2004, pp. 278-280

SUMMARY OF INVENTION

To elucidate at the genetic level of the mechanisms by which a normal cell becomes neoplastic (cancerous) or to analyze the state of the cell during or after the cancerous transformation from a biochemical standpoint, it is sometimes necessary to obtain a specimen of cells having abnormalities in cell division or cell cycle unlike normal cells.

For example, for identifying a gene or a protein (peptide) involved in abnormal cell division of a eukaryotic cell or for finding out a method for correcting abnormalities in cell division, it may be helpful to use, as a specimen, so-called multipolar cells (cells with extra centrosomes or cells with multipolar spindles) in which multipolar spindles, instead of normal bipolar spindles, are formed; in other words, three or more centrosomes (which include fragments of pericentriolar materials (PCM); the same applies hereinafter) are present dispersed in a cell and a spindle (multipolar spindle) is formed randomly extending from the three or more respective dispersed centrosomes serving as spindle poles.

Accordingly, an objective of the present invention is to provide a material and a method for efficiently providing multipolar cells as such a cell specimen.

The present inventors have focused on several peptides reported in Non-Patent Document and Non-Patent Document 2. More specifically, as for peptides to inhibit the activity of the FtsZ (Filamenting temperature-sensitive mutant Z) protein which is present in bacteria (which are prokaryotes) and forms a protein assembly called the Z ring involved in bacterial cell division or for peptides to inhibit the activity of the FtsA (Filamenting temperature-sensitive mutant A) protein, known to work as an to bind the FtsZ protein to cell membranes when coupled to the C-terminus of the FtsZ protein (i.e. for peptides that inhibit the GTPase activity of the FtsZ protein or the ATPase activity of the FtsA protein), they have focused on several peptides (i.e. peptides capable of acting as FtsZ inhibitors or FtsA inhibitors) isolated by employing a general phage display technique.

The present inventors have found out that a supply of these peptides capable of acting as FtsZ inhibitors or FtsA inhibitors to various species of tumor cells (cancer cells) leads to the presence of many centrosomes (which may be PCM) dispersed in the cells, and multipolar cells (cells with extra centrosomes) can be produced, comprising multipolar spindles which are different from dipolar spindles and are formed so as to extend from the many respective dispersed centrosomes serving as spindle poles unlike the way dipolar spindles are formed; and the present invention has been completed.

In the present description, the term "tumor cells" is used to distinguish these cells from normal cells that have not yet become neoplastic. Thus, cells constituting a tumor (typically a cancer) instead of normal cells are called as tumor cells regardless of the origin and nature of the cells.

To achieve the objective, the present invention provides a method described below. In particular, disclosed herein is a method for producing a multipolar cell having three or more centrosomes as well as a multipolar spindle from at least one species of eukaryotic cells (typically cells of humans or animals belonging to mammals, or cells of birds). The method comprises culturing target eukaryotic cells, and supplying the eukaryotic cells being cultured with a synthetic peptide consisting of an amino acid sequence selected from the following amino acid sequences that act as FtsZ, inhibitors or FtsA inhibitors:

(1) CSSATGKSC, (SEQ ID NO: 1)

(2) CLAPSPSKC, (SEQ ID NO: 2)

(3) CLGQTKMRC, (SEQ ID NO: 3)

(4) CGHRPYQYC, (SEQ ID NO: 4)

(5) CWAFPLHHC, (SEQ ID NO: 5)

(6) CTLNSHSNC, (SEQ ID NO: 6)

(7) CEISAKRTC, (SEQ ID NO: 7)

(8) CHILHAQAC, (SEQ ID NO: 8)

```
(9)  CPRPPSLEC,    (SEQ ID NO: 9)

(10) CTGHWASEC,    (SEQ ID NO: 10)

(11) CSYEKRPMC     (SEQ ID NO: 11)
     and

(12) CLTKSYTSC;    (SEQ ID NO: 12)
``` or an amino acid sequence formed by substituting, deleting and/or adding one, two or three amino acid residues in/from/ to the selected amino acid sequence.

According to the method of the present invention having such a constitution, the supply of the synthetic peptide (i.e. a multipolarity-inducing peptide) to cultured cells to a prescribed concentration can lead to formation of 3 or more (typically 5 or more, preferably 8 or more) centrosomes in the cultured cells (typically in M-phase cells) and induce formation of a multipolar spindle having the plurality of centrosomes serving as spindle poles.

Thus, the method of the present invention allows for stable production of multipolar cells (cultured cells) that contribute to identify a gene or a protein (peptide) involved in abnormal cell division of a eukaryotic cell or to find out a method for correcting abnormalities in cell division.

Another preferable embodiment of the method disclosed herein is for producing a multipolar cell having three or more centrosomes as well as a multipolar spindle from at least one species of eukaryotic cells (typically, cells of humans or animals belonging to mammals). The method comprises culturing target eukaryotic cells, and supplying the target eukaryotic cells being cultured with a synthetic peptide consisting of an amino acid sequence selected from the following amino acid sequences that act as FtsZ inhibitors or FtsA inhibitors:

```
(1)  CSSATGKSC,    (SEQ ID NO: 1)

(2)  CLAPSPSKC,    (SEQ ID NO: 2)

(3)  CLGQTKMRC,    (SEQ ID NO: 3)

(4)  CGHRPYQYC,    (SEQ ID NO: 4)

(5)  CWAFPLHHC,    (SEQ ID NO: 5)

(6)  CTLNSHSNC,    (SEQ ID NO: 6)

(7)  CEISAKRTC,    (SEQ ID NO: 7)

(8)  CHILHAQAC,    (SEQ ID NO: 8)

(9)  CPRPPSLEC,    (SEQ ID NO: 9)

(10) CTGHWASEC,    (SEQ ID NO: 10)

(11) CSYEKRPMC     (SEQ ID NO: 11)
     and

(12) CLTKSYTSC;    (SEQ ID NO: 12)
``` or an amino acid sequence formed by substituting, deleting and/or adding one, two or three amino acid residues in/from/ to the selected amino acid sequence; and also an amino acid sequence that constitutes a nucleolar localization signal (NoLS) and is selected from SEQ ID NO: 13 to SEQ ID NO: 20, or an amino acid sequence formed by substituting, deleting and/or adding one two or three amino acid residues in/from/to the selected amino acid sequence.

The present inventors have found out that amino acid sequences known as nucleolar localization signals (NoLS) (see Patent Documents 1, 2 and 3) are involved in transporting peptides front the extracellular space into nuclei (typically nucleoli). By the use of a synthetic peptide constituted to include the amino acid sequence (i.e. a multipolarity-inducing peptide), the peptide can be introduced more efficiently into target cells. Thus, application of the method in the present embodiment will increase the formation efficiency of multipolar cells, allowing for more efficient production and provision of multipolar cells.

In the multipolar cell production method disclosed herein, preferably, the eukaryotic cells to be cultured are synchronized in the G2 phase or M phase and the peptide is supplied to the cultured cells that have been synchronized in the G2 phase or M phase.

By synchronizing the cells to be cultured in the G4 phase or M phase of the cell cycle (blocking the cultured cells in the G2 phase or Ni phase for a certain period of time) and supplying a multipolarity-inducing peptide to the target cultured cells, multipolarity can be induced more efficiently in the cultured cells.

In the multipolar cell production method disclosed herein, suitably, cultured (primary cultured or subcultured) tumor cells are used as the target eukaryotic cells. Particularly preferable target cells include malignant tumor cells (cancer cells) such as cells (cultured cells) derived from a squamous cell carcinoma.

The method disclosed herein can induce multipolarity particularly effectively in cultured tumor cells. Accordingly, the present invention provides a method for inducing multipolarity in tumor cells (i.e. a cell in which three or more centrosomes have formed) characterized by supplying a synthetic peptide disclosed herein to cultured tumor cells The present invention can provide a multipolar cell produced by a method disclosed herein. Multipolar cells (cells with extra centrosomes) provided by the present invention comprises 3 or more (typically 5 or more, preferably 8 or more) centrosomes formed therein, and preferably also a multipolar spindle formed therein having the plurality of centrosomes serving as spindle poles. The multipolar cells can preferably remain viable in the multipolar state for a few or more days (typically, 5 or more days, e.g. 5 days to 14 days) without undergoing cell division.

DESCRIPTION OF EMBODIMENTS

Figure 1:
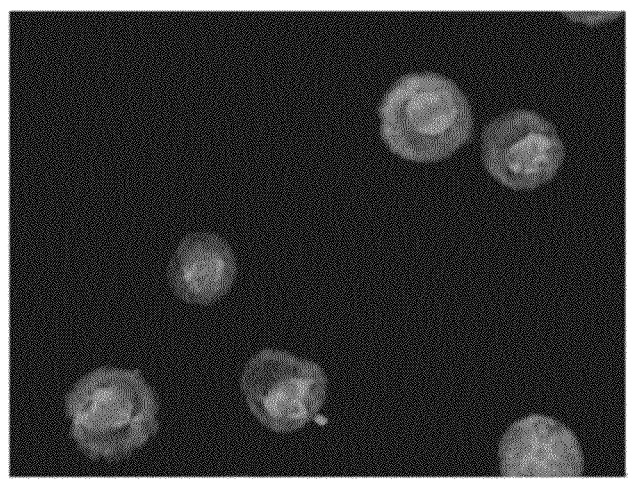
FIG. 1 is a fluorescence microscope photo (image) showing the state of cultured cells after incubation following addition of a sample peptide (Sample 9) to a culture medium of HeLa cells (synchronized in the G2 phase (or M phase) of the cell cycle by nocodazole treatment) to a peptide concentration in the culture medium of 10 µM, with the photo being a merged image of a DAN nuclear stain image and a fluorescence image showing the result of an immunofluorescence assay using an anti-tubulin antibody.

Preferred embodiments of the present invention are described below. Note that technical matters other than the matters particularly mentioned in the present description (e.g. primary structures of synthetic peptides disclosed herein) which are required for carrying out the present invention (e.g. general matters relating to chemical peptide synthesis, cell cultivation, and preparation of a pharmaceutical composition containing a peptide) are matters of design variation that could be apprehended by a person skilled in the art based on conventional art in such fields as cell engineering, physiology, medicine, pharmacology organic chemistry, biochemistry, genetic engineering, protein engineering, molecular biology, genetics, and the like. The present invention can be practiced based on the technical details disclosed in the present description and common general technical knowledge in the pertinent fields. In the following description, amino acids are indicated by single-letter designations (in sequence listings, by three-letter designations) in accordance with the nomenclature for amino acids set forth in the IUPAC-IUB guidelines.

The present description incorporates by reference the entire contents of all the documents cited herein.

In the present description, the term "synthetic peptide" refers to a peptide fragment that is manufactured by artificial chemical synthesis or biosynthesis (i.e. genetic engineering-based production).

In this description, the term "peptide" refers to an amino add polymer having a plurality of peptide bonds, and is not limited by the number of amino acid residues included in the peptide chain, with the term typically referring to one having a relatively small molecular weight with a total of no more than 50 (e.g. no more than 30) amino acid residues.

In this description, unless otherwise specified, the term "amino acid residue" includes the N-terminal amino acid and the C-terminal amino acid of a peptide chain.

In this description, the term "tumor" should be interpreted in a broad sense and refers to general tumors (typically malignant tumors) including carcinomas and sarcomas as well as lesions of blood and hematopoietic tissue (leukemia, lymphoma, etc.). The term "tumor cells" refers to cells that form such a tumor, typically referring to cells that have come to undergo abnormal proliferation with no relation to surrounding normal tissue (i.e. cells that have become cancerous). Thus, unless otherwise specified, cells classified as tumor cells (cancer cells) instead of normal cells are called as tumor cells regardless of the origin and nature of the cells. The concept of tumor cells referred to herein encompasses cells that form epithelial tumors (squamous cells carcinoma, adenocarcinoma, etc.), nonepithelial tumors (various types of sarcoma, osteosarcoma, etc.), various types of cytoma (neuroblastoma, retinoblastoma, etc.), lymphomas, melanomas, and so on.

In this description, the term "modified amino acid sequence" regarding a certain amino acid sequence refers to an amino acid sequence formed by substituting, deleting and/or adding (inserting) ting) one or several (e.g. two or three) amino acid residues without impairing the function of the certain amino acid sequence (e.g. the ability of the multipolarity-inducing peptides to induce multipolarity, the NoLS's transportability from the extracellular space into nuclei). Typical examples of the modified amino acid sequence referred to in the present description include a sequence generated by conservative amino acid replacement where one or several (typically two or three) amino acid residues are conservatively substituted (e.g., a sequence where a basic amino acid residue has been substituted with a different basic amino acid residue; e.g. mutual substitution between a lysine residue and an arginine residue), a sequence obtained by adding (inserting) or deleting one or several (typically two or three) amino acid residues in a certain amino acid sequence, and the like. Thus, the multipolarity-inducing peptide disclosed herein encompasses synthetic peptides consisting of amino acid sequences identical to the amino acid sequences of the respective SEQ ID NOs as well as a synthetic peptide consisting of an amino acid sequence resulting from substitution (e.g. the conservative substitution), deletion and/or addition of one or several (typically two or three) amino acid residues in/from/to the amino acid sequence of each SEQ ID NO while showing comparable multipolarity-inducing activity.

In this description, the term "polynucleotide" refers to a polymer (nucleic acids) in which several nucleotides are linked by phosphodiester bonds, but not limited by the number of nucleotides. The polynucleotide in the present description encompasses DNA fragments and RNA fragments of various lengths. The term "artificially designed polynucleotide" refers to a polynucleotide whose chain the whole length) does not exist by itself in nature and that is manufactured artificially by chemical synthesis or biosynthesis (i.e., genetic engineering-based production).

The present invention also provides a composition preferably used for practicing the multipolar cell production method disclosed herein. In other words, the composition disclosed herein is a composition (which may be referred to as a "multipolarity-inducing composition" hereinafter) comprising at least one species of pharmaceutically acceptable carrier, and further comprising, as an active ingredient, a multipolarity-inducing peptide consisting of an amino acid sequence which has been found for the first time by the present inventors to have an activity to induce multipolarity in certain eukaryotic cells typically, cells of mammals including humans and other animals, or cells of birds, preferably cultured tumor cells) described earlier or an NoLS-coupled multipolarity-inducing peptide constituted by coupling an NoLS to the N-terminus or the C-terminus of the amino acid sequence of the peptide. It is also referred to as a multipolarity-inducing agent.

Some of the multipolarity-inducing peptides disclosed herein are each constituted with an amino acid sequence represented by one of SEQ ID NO: 1 to SEQ ID NO: 12 (or a modified sequence thereof). As described earlier, the peptides consisting of these amino acid sequences can act as FtsA inhibitors (SEQ ID NOs: 1 to 10) or FtsZ inhibitors (SEQ ID NOs: 11 to 12) against certain species of bacteria as reported in Non-Patent Document 1 or Non-Patent Document 2 listed earlier. Heretofore, however, such various peptides capable of acting as FtsA inhibitors or FtsZ inhibitors have never been known to induce multipolarity in certain cells (typically tumor cells), or nothing has ever suggested this, either.

Some others of the multipolarity-inducing peptides disclosed herein are each constituted with an amino acid sequence represented by one of SEQ ID NO: 1 to SEQ ID NO: 12 (or a modified sequence thereof) as well as an amino acid sequence forming an NoLS represented by one of the following SEQ ID NO: 13 to SEQ ID NO: 20 (or a modified sequence thereof):

(13) KKRTLRKNDRKKR, (SEQ ID NO: 13)

(14) WRRQARFK, (SEQ ID NO: 14)

(15) RSRKYTSWYVALKR, (SEQ ID NO: 15)

(16) MAKSIRSKHRRQMRMMKRE, (SEQ ID NO: 16)

(17) MARRRRHRGPRRPRPP, (SEQ ID NO: 17)

(18) GRCRRLANFGPRKRRRRRR, (SEQ ID NO: 18)

(19) RRRKRNRDARRRRRKQ (SEQ ID NO: 19)
and

(20) MQRKPTIRRKNLRLRRK. (SEQ ID NO: 20)

These amino acid sequences listed are all known as NoLS, and their data can be obtained, for example, from the database of amino acid sequences of protein provided by NCBI (National Center for Biotechnology Information).

Namely, the amino acid sequence of SEQ ID NO: 13 corresponds to an NoLS consisting of 13 amino acid residues from, amino acid residue 491 to amino acid residue 503 of LIM kinase 2 present in human endothelial cells, which is a type of protein kinase involved in intracellular signal transduction.

The amino acid sequence of SEQ ID NO: 14 corresponds to an NoLS consisting of 8 amino acid residues contained in the N protein (nucleocapsid protein) of IBV (avian infectious bronchitis virus) which belongs to the genus Coronavirus.

The amino acid sequence of SEQ 11) NO 15 corresponds to an NoLS consisting of 14 total amino acid residues originating from FGF2 (fibroblast growth factor 2).

The amino acid sequence of SEQ ID NO: 16 corresponds to an NoLS consisting of 19 total amino acid residues originating from a species of nucleolar protein (ApLLP).

The amino acid sequence of SEQ ID NO: 17 corresponds to an NoLS consisting of 16 total amino acid residues originating from a protein (γ(1)34.5) of HSV-1 (herpes simplex virus type 1).

The amino acid sequence of SEQ ID NO: 18 corresponds to an NoLS consisting of 19 total amino acid residues originating from p48 protein of HIC (human I-mfa domain-containing protein).

The amino acid sequence of SEQ ID NO: 19 corresponds to an NoLS consisting a 16 total amino acid residues originating from MEQ protein of MDV (Marek's disease virus).

The amino acid sequence of SEQ ID NO: 20 corresponds to an NoLS consisting of 17 total amino acid residues originating from survivin-deltaEx3 which is an apoptosis-suppressing protein.

By placing the NoLS species represented by one of these SEQ ID NOs on the N-terminal side or the C-terminal side of the amino acid sequence represented by one of SEQ ID NO: 1 to SEQ ID NO 12 (or a modified sequence thereof), a preferable multipolarity-inducing peptide (synthetic peptide) can be constituted.

The multipolarity-inducing peptide disclosed herein preferably has at least one amidated amino acid residue. Amidation of a carboxyl group in an amino acid residue (typically the C-terminal amino acid residue of the peptide chain) may increase the structural stability (e.g., protease resistance) of the synthetic peptide.

The multipolarity-inducing peptide disclosed herein is short in the chain length, having a relatively small number of amino acid residues (typically 30 or fewer). Thus, its chemical synthesis is facile and the multipolarity-inducing peptide can be easily provided. With respect to the conformation (spatial structure) of the peptide, there are no particular limitations as long as it exhibits the multipolarity-inducing activity. From the standpoint of unlikeliness to become a an immunogen (antigen), a preferable peptide has a linear or a helical structure. Peptides having these conformations are less likely to form epitopes. From such a standpoint, it is preferable as a peptide used for manufacturing a multipolarity-inducing composition disclosed herein.

It is noted that in the multipolarity-inducing peptide disclosed herein, all amino acid residues are preferably L-amino acids while for as long as the multipolarity-inducing activity is not lost, part or all of the amino acid residues may be substituted with D-amino acids.

The multipolarity-inducing peptide disclosed herein can be easily manufactured according to general chemical synthesis methodologies. For instance, any of conventional solid-phase and liquid-phase synthetic methods can be employed. A preferable solid-phase synthetic method uses Boc (t-butyloxycarbonyl) or Fmoc (9-fluorenylmethoxycarbonyl) as the protecting group for the amino group.

For the multipolarity-inducing peptide disclosed herein, a peptide chain having a desired amino acid sequence and a portion with modification (e.g., C-terminal amidation, etc.) can be synthesized by solid-phase synthesis using a commercial peptide synthesizer (which is, for instance, available from PerSeptive Biosystems, Applied Biosystems, etc.).

Alternatively, the multipolarity-inducing peptide may be biosynthesized based on genetic engineering techniques. In particular, a polynucleotide (typically a DNA strand) is synthesized so as to have a nucleotide sequence (including the ATG initiation codon) encoding the amino acid sequence of the desired multipolarity-inducing peptide. Then, in accordance with the host cells, a recombinant vector is constructed so as to have an expression gene construct composed of the synthesized polynucleotide (DNA) and various regulatory elements (including promoters, ribosome binding sites, terminators, enhancers, and various cis-elements which control the expression level) to allow expression of the amino acid sequence within the host cells.

By an ordinary technique, this recombinant vector is inserted into prescribed host cells (e.g. yeasts, insect cells, plant cells), and the host cells, or tissue or a mass containing these cells are cultured under specific conditions. In this way, the target peptide can be expressed and produced intracellularly. The target multipolarity-inducing peptide can be obtained by isolating the peptide from the host cells (from the culture medium if secreted) and subjecting it to refolding, purification, and so on as necessary.

Methods hitherto used in the art may be directly employed without modification as the method for constructing the recombinant vector, introducing the constructed recombinant vector into the host cell, and so on. Because such methods themselves are not distinctive to the present invention, detailed description is omitted here.

For example, a fusion protein expression system may be employed to allow efficient large-scale production in host cells. In particular, a gene (DNA) coding for the amino acid sequence of the multipolarity-inducing peptide of interest is chemically synthesized, and the synthesized gene is introduced to a preferred site on a suitable fusion protein expression vector (e.g. GST (glutathione S-transferase) fusion protein expression vectors such as the pET series available from Novagen as well as the pGEX series available from Amersham Bioscience). Host cells (typically, *Escherichia coil*) are then transformed by the vector. The resulting transformant is cultured to produce the target fusion protein. This protein is then extracted and purified. Subsequently, the purified fusion protein is cleaved with a specific enzyme (protease), and the liberated target peptide fragments (the designed multipolarity-inducing peptide) are collected by a method such as affinity chromatography. As necessary, it is allowed to refold by a suitable method. The multipolarity-inducing peptide disclosed herein can be produced by using such a fusion protein expression system heretofore known (e.g., the GST/His system available from Amersham Bioscience may be used).

Alternatively, the target polypeptide may be synthesized in vitro by constructing a template DNA for a cell-free protein synthesis system (i.e., a synthesized gene fragment having a nucleotide sequence that codes for the amino acid sequence of the multipolarity-inducing peptide), and employing a cell-free protein synthesis system with use of various compounds (e.g., ATP, RNA polymerase, amino acids, etc.) required for the peptide synthesis. For information concerning cell-free protein synthesis systems, reference may be made to, for example, Shimizu et al., *Nature Biotechnology,* 19, 751-755 (2001), and Madin et al., *Proc. Natl. Acad. Sci. USA,* 97(2), 559-564 (2000). Based on the technology described in these articles, many corporations have been conducting contract manufacturing of polypeptides at the time when this application was filed. Also, wheat germ cell-free protein synthesis kits (such as PROTEIOS™ available from Toyobo Co., Ltd. of Japan) are commercially available.

A heretofore known method can be employed for facile production (synthesis) of a single-stranded or double-stranded polynucleotide containing a nucleotide sequence encoding the multipolarity-inducing peptide disclosed herein and/or a nucleotide sequence complementary thereto. In other words, by selecting a codon corresponding to the respective amino acid residues constituting the designed amino acid sequence, a nucleotide sequence corresponding to the amino acid sequence of the multipolarity-inducing peptide can be easily determined and provided. Once the nucleotide sequence is determined, by utilizing a DNA synthesizer, etc., can be easily obtained a polynucleotide (single strand) corresponding to the desired nucleotide sequence. Furthermore, the target double-stranded DNA can be obtained by using the resulting single-stranded DNA as a template and employing various enzymatic synthetic methods (typically PCR). The polynucleotide may be in the form of DNA or RNA (mRNA, etc.). The DNA can be provided as a double strand or a single strand. When it is provided as a single strand, it may be a coding strand (sense strand) or an anticoding strand (anti-sense strand) complementary thereto.

The polynucleotide obtained in such a way can be used as a material for constructing a recombinant DNA (expression cassette) for producing the multipolarity-inducing peptide in various host cells or in a cell-free protein synthesis system.

The multipolarity-inducing peptide disclosed herein can act on at least one species of eukaryotic cells (preferably tumor cells of mammals or birds) causing formation of many centrosomes (typically, 3 or more, preferably 5 or more, particularly preferably 8 or more, even more preferably 10 or more e.g. about 3 to 20 centrosomes per cell) in the cells (typically in the M phase), thereby inducing formation of a corresponding number of multipolar spindles.

The multipolarity-inducing peptide may be in a salt form as far as the multipolarity-inducing activity is not impaired. For example, it is possible to use an acid salt of the peptide, which can be obtained by adding a commonly used inorganic or organic acid in accordance with an ordinary technique. Alternatively, while the multipolarity-inducing activity is maintained, a different type of salt (e.g., a metal salt) can be used. Accordingly, the scope of the "peptide" described in this description and in claims encompasses such salt forms.

The multipolarity-inducing composition disclosed herein may contain various pharmaceutically (medically) acceptable carriers in accordance with the preparation, as far as it can preserve the multipolarity-inducing peptide which is active ingredient without losing its ability to induce the multipolarity. For example, carriers generally used as diluents or excipients in peptide medications can be utilized.

Although the carrier may suitably vary depending or the intended purpose and form of the composition disclosed herein (i.e. a multipolarity-inducing composition), typical examples include water, physiological buffers and various organic solvents. The carrier may be an aqueous alcohol (ethanol or the like) solution at an appropriate concentration, glycerol, or non-drying oil such as olive oil. Alternatively, it may be liposome. Examples of secondary ingredients that may be contained in the multipolarity-inducing composition include various fillers, hulking agents, binders, wetting agents, surfactants, dyes, fragrances and the like.

Typical examples of the form of the multipolarity-inducing composition (multipolarity-inducing drug) include liquid formulations, suspensions, and so on. The multipolarity-inducing composition may be formulated as a freeze-dried product or pellets to prepare a drug solution by dissolving in saline or a suitable buffer (e.g., PBS) just prior to use.

The process itself of preparing a composition in various forms with the multipolarity-inducing peptide (primary ingredient) and various carriers (secondary ingredients) may be carried out in accordance with a heretofore known method. Because such a preparation process itself is not distinctive to the present invention, detailed description is omitted here.

The target cells to which the multipolarity-inducing peptide disclosed herein is applied are not particularly limited as long as they are eukaryotic cells (cultured cells) and are susceptible to multipolarity induction. The composition can be applied to various types of cells of humans and nonhuman mammals or cells of birds, especially to cultured tumor cells (various cell lines). Examples include cells forming squamous cell carcinomas, cells forming adenocarcinomas, and cells (cultured cells) forming cytomas such as neuroblastomas, retinoblastomas, pheochromocytomas, and other cytomas.

No special treatment is required for the method for supplying the multipolarity-inducing peptide (multipolarity-inducing composition) disclosed herein to target cultured cells. For example, a suitable amount of the multipolarity-inducing peptide (or a composition comprising the peptide as the primary component) can be added to a culture (typically a culture medium) in which the target cells (including a cell aggregation, tissue or an organ removed from a living organism) are being cultured.

The amount of the peptide per dose and the number of doses can be decided by considering efficiency of multipolarity induction of the cells in the culture, and are not particularly limited as they may vary in accordance with conditions such as the typo of tumor cells to be cultured, cell density (cell density at the incubation start), passage number, incubation conditions, type of culture medium, and so on. It may be adjusted so that the concentration of multipolarity-inducing peptide in the culture medium is in a range of about 1 µM or higher, but lower than 20 µM or preferably 5 µM or higher, but 100 µM or lower. Addition of an excessively small amount of the peptide is not preferable because the multipolarity induction rate of the cells in the culture will be too low. On the other hand, addition of an excessively large amount of the peptide is not preferable because an excessive level of multipolarity induction will cause cell death prematurely.

The multipolar cell production method (multipolarity induction method) disclosed herein is preferable since the target cultured cells are synchronized in the cell cycle in advance and by supplying a desirable multipolarity-inducing peptide to the synchronized cells, the multipolar level of the cells in the culture can be increased. In particular, it is preferable that cells in a culture are synchronized in the G2 phase or M phase.

Herein, "being synchronized in the G2 phase or M phase" means that by subjecting cultured cells to a suitable treatment (typically, addition of a drug such as nocodazole, etc., generally used for cell cycle synchronization), the transition of the cultured cells from the G2 phase to the M phase or from the M phase to the G1 phase is inhibited and the cells are arrested in the G2 phase or M phase. For example, nocodazole, colchicine, colcemid, vincristine or the like can be added to a cell culture (typically a culture medium) to a suitable concentration to adjust the cell cycle, thereby synchronizing the target cells in the G2 phase or M phase. It is particularly preferable to supply a multipolarity-inducing peptide in synchrony with the G2 phase.

Alternatively, general double thymidine block or the like can be employed to synchronize cultured cells it the G1 phase of the cell cycle (i.e. to inhibit the transition from the G1 phase to the S phase).

Several worked examples relating to the present invention are described below while these examples are not intended to limit the scope of the invention.

Example 1

Peptide Synthesis

A total of 24 different synthetic peptides consisting of the respective amino acid sequences shown in Table 1 were produced using a peptide synthesizer. In the following description, the 24 in total of different peptides synthesized are referred to as Samples 1 to 24.

TABLE 1

| Sample No. | Amino acid sequence | Total number of amino acid residues |
|---|---|---|
| 1 | CSSATGKSC (SEQ ID NO: 1) | 9 |
| 2 | CLAPSPSKC (SEQ ID NO: 2) | 9 |
| 3 | CLGQTKMRC (SEQ ID NO: 3) | 9 |
| 4 | CGHRPYQYC (SEQ ID NO: 4) | 9 |
| 5 | CWAFPLHHC (SEQ ID NO: 5) | 9 |
| 6 | CTLNSHSNC (SEQ ID NO: 6) | 9 |
| 7 | CEISAKRTC (SEQ ID NO: 7) | 9 |
| 8 | CHILHAQAC (SEQ ID NO: 8) | 9 |
| 9 | CPRPPSLEC (SEQ ID NO: 9) | 9 |
| 10 | CTGHWASEC (SEQ ID NO: 10) | 9 |
| 11 | CSYEKRPMC (SEQ ID NO: 11) | 9 |
| 12 | CLTKSYTSC (SEQ ID NO: 12) | 9 |
| 13 | CSSATGKSCKKRTLRKNDRKKR (SEQ ID NO: 21) | 22 |
| 14 | CLAPSPSKCKKRTLRKNDRKKR (SEQ ID NO: 22) | 22 |
| 15 | CLGQTKMRCKKRTLRKNDRKKR (SEQ ID NO: 23) | 22 |
| 16 | CGHRPYQYCKKRTLRKNDRKKR (SEQ ID NO: 24) | 22 |
| 17 | CWAFPLHHCKKRTLRKNDRKKR (SEQ ID NO: 25) | 22 |
| 18 | CTLNSHSNCKKRTLRKNDRKKR (SEQ ID NO: 26) | 22 |
| 19 | CEISAKRTCKKRTLRKNDRKKR (SEQ ID NO: 27) | 22 |
| 20 | CHILHAQACKKRTLRKNDRKKR (SEQ ID NO: 28) | 22 |
| 21 | CPRPPSLECKKRTLRKNDRKKR (SEQ ID NO: 29) | 22 |
| 22 | CTGHWASECKKRTLRKNDRKKR (SEQ ID NO: 30) | 22 |

TABLE 1-continued

| Sample No. | Amino acid sequence | Total number of amino acid residues |
|---|---|---|
| 23 | CSYEKRPMCKKRTLRKNDRKKR (SEQ ID NO: 31) | 22 |
| 24 | CLTKSYTSCKKRTLRKNDRKKR (SEQ ID NO: 32) | 22 |

Each sample is constituted to have an amino acid sequence shown in Table 1 (also in the sequence listing). More specifically, Samples 1 to 12 are peptides capable of acting as FtsA inhibitors (SEQ ID NOs: 1 to 10) or FtsZ inhibitors (SEQ ID NOs: 11 to 12) disclosed in Non-Patent Document 1 or in Non-Patent Document 2; and each one is a synthetic peptide consisting of 9 total amino acid residues, characterized by the N-terminal and C-terminal amino acid residues being cysteine residues.

Samples 13 to 24 are synthetic peptides each consisting of 22 total amino acid residues, characterized by the amino acid sequence of each peptide of Samples 1 to 12 being coupled at the C-terminal side with the amino acid sequence constituting the NoLS of SEQ ID NO: 13.

All peptides were synthesized by solid-phase synthesis (Fmoc chemistry) using a commercial peptide synthesizer (an Intavis AG system) in accordance with its operation manual. Because the mode of using the peptide synthesizer itself is not distinctive to the present invention, detailed description is omitted here.

Each sample synthesized was dissolved in PBS (phosphate buffered saline) to prepare a stock solution having a peptide concentration of 1 mM.

Example 2

Multipolarity-Inducing Activity Assay 1 for Each Synthetic Peptide

Some of the sample peptides obtained in Example 1 were tested for multipolarity-inducing activity against target cultured tumor cells. Details of the assay are as described below.

As the tumor cells tested, a HeLa cell line (HeLa S3) was used. The cell line was cultured beforehand in a DMEM medium (i.e. Dulbecco MEM medium (DMEM medium, a Gibco product) containing 10% fetal bovine serum (FBS, a Gibco product), 2 mM of L-glutamine, 50 unit/mL of penicillin, and 50 µg/mL of streptomycin), and seeded at about $3 \times 10^4$ cells per well in an 8-well slide glass. Thymidine was added to the culture medium to a final concentration of 2.5 mM. Incubation was carried out at 37° C. under 5% $CO_2$ for 16 hours. The culture medium was exchanged to remove thymidine and incubation was carried out for 8 more hours. Subsequently, thymidine was added again to a final concentration of 2.5 mM and incubation was carried out for 16 hours.

By such double thymidine block, the cells being cultured were synchronized in the G1 phase of the cell cycle. After such synchronization treatment, the culture medium was exchanged to remove thymidine and incubation was carried out for 2 more hours. Subsequently, one of the sample peptides was added to each well. In this example, one of Samples 1, 4, 8, 9, 12 and 14 was added to a peptide concentration in the well of 10 µM.

After a sample peptide was added as described above, the 8-well slid glass was incubated under the aforementioned conditions for 6 hours.

After 6 hours of incubation, the presence of multipolarity was observed by immunofluorescence under fluorescence microscope. In particular, after 6 hours of incubation following the addition of a sample peptide, the cultured cells were subjected to nuclear staining with DAPI (4',6-diamidino-2-phenylindole), and using α-tubulin as a marker for spindles, the cells were tested for the presence of tubulin (i.e., the presence of spindles) by immunofluorescence with an anti-tubulin antibody (primary antibody) to identify the tubulin and a fluorescent dye (ALEXA FLUOR (registered trademark) 555)-labeled secondary antibody to identify the primary antibody.

Table 2 shows the multipolar levels (% of the number of multipolar cells in which a spindle (multipolar spindle) was found randomly extending from each of 3 or more centrosomes relative to the number of M-phase cells observed under fluorescence microscope) computed based on the fluorescence microscope observations.

TABLE 2

| Sample No. (Concentration) | Number of M-phase cells | Number of multipolar cells | Multipolar level (%) |
|---|---|---|---|
| 1 (10 µM) | 84 | 7 | 8.3 |
| 4 (10 µM) | 60 | 6 | 10.0 |
| 8 (10 µM) | 103 | 11 | 10.7 |
| 9 (10 µM) | 102 | 19 | 18.6 |
| 12 (10 µM) | 100 | 13 | 13.0 |
| 14 (10 µM) | 74 | 10 | 13.5 |
| Control (no added peptide) | 115 | 4 | 3.5 |

As shown in Table 2, when compared to the multipolar level of 3.5% in the control group with no added sample peptide, the multipolar levels increased (8.3 to 18.6%) in the treated groups with an added sample peptide. In particular, in the group supplemented with Sample 4, 8, 9, 12 or 14, multipolarity was observed in 10% or more (preferably 15% or more) of the M-phase cells.

Example 3

Multipolarity-Inducing Activity Assay 2 for Each Synthetic Peptide

The same sample peptides as those used in Example 2 above were used and tested for multipolarity-inducing activity against cultured tumor cells synchronized in the G2 phase (or M phase). Details of the assay are as described below.

As the tumor cells tested, a HeLa cell line (HeLa S3) was used. The cell line was cultured under the same conditions as Example 2 and seeded at about $3 \times 10^4$ cells per well in an 8-well slide glass. Thymidine was added to the culture medium to a final concentration of 2.5 mM. Incubation was carried out at 37° C. under 5% $CO_2$ for 18 hours. The culture medium was exchanged to remove thymidine and incubation was carried out for 6 more hours. Subsequently, nocodazole was added to a final concentration of 0.1 µg/mL and incubation was carried out for 16 hours. By such addition of nocodazole, the cells being cultured were synchronized in the G2 phase (M phase) of the cell cycle.

After the 16 hours of incubation, without exchanging the culture medium (i.e. with nocodazole being contained), one of the sample peptides was added to each well to a peptide concentration in the well of 10 µM and incubation was carried out for 4 hours. Subsequently, the culture medium was exchanged and incubation was continued for 2 more hours without nocodazole or the sample peptide.

After the 2 hours of incubation, in the same manner as Example 2, the presence of multipolarity was observed by immunofluorescence under fluorescence microscope.

Table 3 shows the multipolar levels (% of the number of multipolar cells in which a spindle (multipolar spindle) was found randomly extending from each of 3 or more centrosomes relative to the number of M-phase cells observed under fluorescence microscope) computed based on the fluorescence microscope observations.

TABLE 3

| Sample No. (Concentration) | Number of M-phase cells | Number of multipolar cells | Multipolar level (%) |
|---|---|---|---|
| 1 (10 μM) | 75 | 47 | 62.7 |
| 4 (10 μM) | 75 | 47 | 62.7 |
| 8 (10 μM) | 75 | 51 | 68.0 |
| 9 (10 μM) | 75 | 55 | 73.3 |
| 12 (10 μM) | 75 | 48 | 64.0 |
| 14 (10 μM) | 75 | 46 | 61.3 |
| Control (no added peptide) | 75 | 2 | 2.7 |

Figure 2:
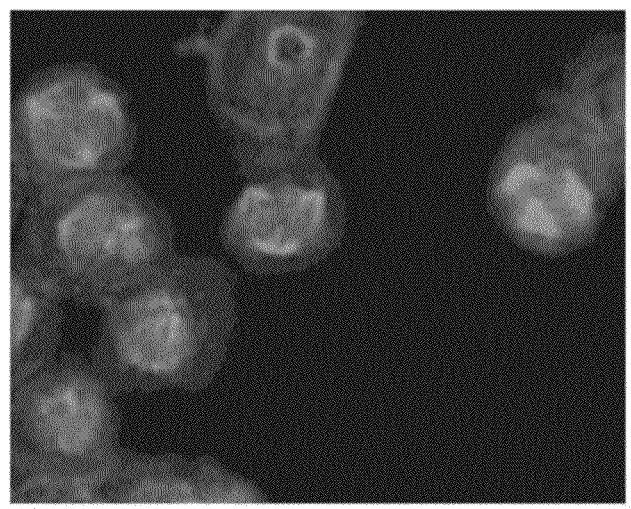
FIG. 2 is a fluorescence microscope photo (image) showing the state of cultured cells after incubation following addition of a sample peptide (Sample 12) to a culture medium of HeLa cells (synchronized in the G2 phase (or M phase) of the cell cycle by nocodazole treatment) to a peptide concentration in the culture medium of 10 μM, with the photo being a merged image of a DAPI nuclear stain image and a fluorescence image showing the result of an immunofluorescence assay using an anti-tubulin antibody.
Figure 3:
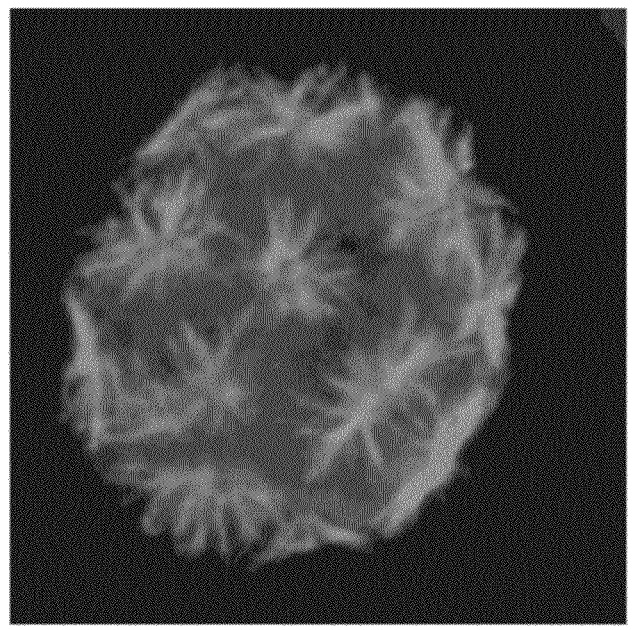
FIG. 3 is a fluorescence microscope photo (image) showing the state of a cultured cell after incubation following addition of a sample peptide (Sample 9) to a culture medium of HeLa cells (synchronized in the G2 phase (or M phase) of the cell cycle by nocodazole treatment) to a peptide concentration in the culture medium of 10 μM, with the photo being a merged image of a DAPI nuclear stain image and a fluorescence image showing the result of an immunofluorescence assay using an anti-tubulin antibody. This image shows a cell with a particularly high degree of multipolarity.

As shown in Table 3, when compared to the multipolar level of 2.7% in the control group with no added sample peptide, significantly higher multipolar levels (61.3 to 73.3%) were observed in all the treated groups with an added sample peptide. This indicates that synchronization of target culture cells in the G2 phase (or M phase) leads to significantly higher multipolarity-inducing activity by a multipolarity-inducing peptide. As some examples, the results of fluorescence microscope observations relating to Samples 9 and 12 are shown in FIG. 1 to FIG. 3. As shown in the fluorescence microscope images of the treated groups with added Sample 9 (FIG. 1, FIG. 3) and Sample 12 (FIG. 2), 3 or more centrosomes formed in many cells and many cells were accordingly observed to have multipolar spindles formed therein.

Example 4

Multipolarity-Inducing Activity Assay 3 for Each Synthetic Peptide

Some of the sample peptides obtained in Example 1 were tested for multipolarity-inducing activity against target cultured tumor cells. Details of the assay are as described below. As the tumor cells tested, cells forming a human squamous cell carcinoma (human alveolar basal epithelial adenocarcinoma cells, A549) were used. The cell line was cultured in the same manner as Example 2 described above. The resulting cultured tumor cells were synchronized in the G2 phase (or M phase) in the same manner as Example 3 described above. Similarly to Examples 2 and 3 described above (although the number of M-phase cells was 100), the presence of multipolarity was observed by immunofluorescence under fluorescence microscope. In addition, using centrin-2 as a marker for centrosomes (centrioles), the cells were tested for the presence of centrin-2 (i.e. the presence of centrosomes) by immunofluorescence with an anti-centrin-2 antibody (primary antibody) to identify the centrin-2 and a fluorescent dye-labeled secondary antibody to identify the primary antibody.

Table 4 shows the multipolar levels of the number of multipolar cells in which a spindle multipolar spindle) was found randomly extending from each of 3 or more centrosomes relative to the number of M-phase cells observed under fluorescence microscope) computed based on the fluorescence microscope observations.

TABLE 4

| Sample No. (Concentration) | Multipolar level (%) |
|---|---|
| 1 (10 μM) | 42 |
| 2 (10 μM) | 38 |
| 3 (10 μM) | 44 |
| 4 (10 μM) | 36 |
| 5 (10 μM) | 41 |
| 6 (10 μM) | 30 |
| 7 (10 μM) | 36 |
| 8 (10 μM) | 36 |
| 9 (10 μM) | 43 |
| 10 (10 μM) | 31 |
| 11 (10 μM) | 61 |
| 12 (10 μM) | 45 |
| 14 (10 μM) | 38 |
| 19 (10 μM) | 44 |
| Control (no added peptide) | ≤3 |

As shown in Table 4, when compared to the multipolar level of 3% or lower in the control group with no added sample peptide, higher multipolar levels (30 to 61%) were observed in all the treated groups with an added sample peptide. In particular, in the cells supplemented with the peptide of Sample 1, 3, 5, 9, 11 or 12, or with the NoLS-coupled peptide of Sample 19, the multipolar level was significantly high at 40% or above.

Figure 4:
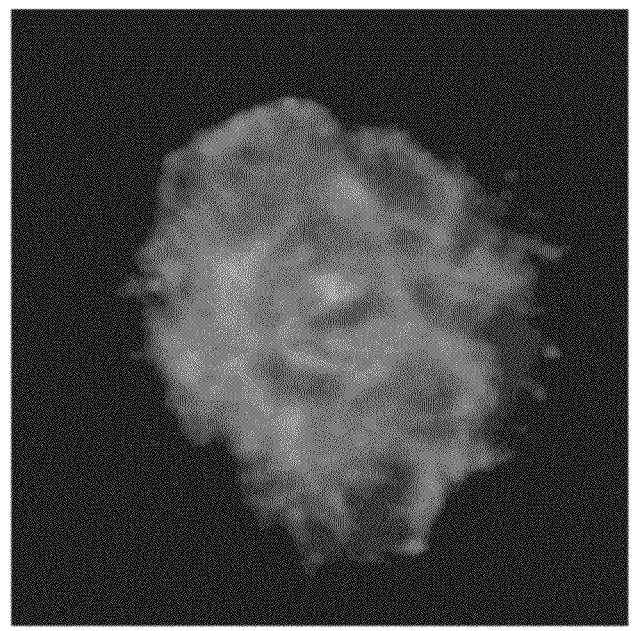
FIG. 4 is a fluorescence microscope photo (image) showing the state of a cultured cell after incubation following addition of a sample peptide (Sample 6) to a culture medium of A549 cells (synchronized in the G2 phase (or M phase) of the cell cycle by nocodazole treatment) to a peptide concentration in the culture medium of 10 μM, with the photo being a merged image of a DAPI nuclear stain image and a fluorescence image showing the result of an immunofluorescence assay using a fluorescence-labeled anti-tubulin antibody and an anti-centrin antibody.
Figure 5:
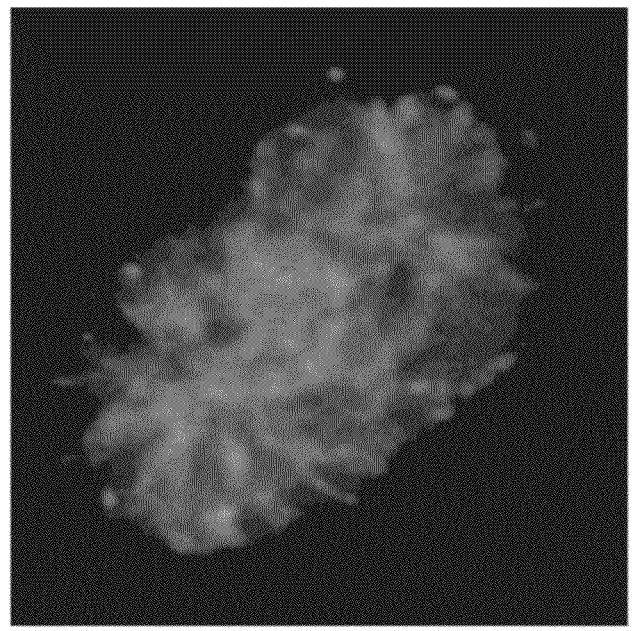
FIG. 5 is a fluorescence microscope photo (image) showing the state of a cultured cell after incubation following addition of a sample peptide (Sample 11) to a culture medium of A549 cells (synchronized in the G2 phase (or M phase) of the cell cycle by nocodazole treatment) to a peptide concentration in the culture medium of 10 μM, with the photo being a merged image of a DAN nuclear stain image and a fluorescence image showing the result of an immunofluorescence assay using a fluorescence-labeled anti-tubulin antibody and an anti-centrin antibody.

As some examples, the results of fluorescence microscope observations relating to Samples 6 and 11 are shown in FIG. 4 and FIG. 5. As shown in the fluorescence microscope images of the treated groups with added Sample 6 (FIG. 4) and Sample 11 (FIG. 5), 3 or more (typically 4 or more, e.g. 8 or more) centrosomes formed in many cells and many cells were accordingly observed to have multipolar spindles formed therein. Hence, the peptide disclosed herein can suitably induce multipolarity in cultured tumor cells (e.g. cells derived from a squamous cell carcinoma) and allows for stable production of multipolar cells (cultured cells).

INDUSTRIAL APPLICABILITY

As described above, according to the multipolarity-inducing peptide disclosed herein, it is possible to frequently induce multipolarity in target cultured cells (typically tumor cells), and to provide multipolar cells that can contribute as a research material to various research purposes (e.g. search for a factor involved in cell division or mechanism elucidation).

[Sequence Listing Free Text]
SEQ ID NOs: 1 to 12, 21 to 32 synthetic peptides
[Sequence Listng]
TG12-007PCT_ST25.txt

The invention claimed is:

1. A method for producing from at least one species of eukaryotic cells a multipolar cell having three or more centrosomes and a multipolar spindle, the method comprising culturing target eukaryotic cells, and
supplying the eukaryotic cells being cultured with a synthetic peptide consisting of an amino acid sequence selected from the following amino acid sequences that act as FtsZ inhibitors or FtsA inhibitors:

(1) CSSATGKSC, (SEQ ID NO: 1)

(2) CLAPSPSKC, (SEQ ID NO: 2)

(3) CLGQTKMRC, (SEQ ID NO: 3)

(4) CGHRPYQYC, (SEQ ID NO: 4)

(5) CWAFPLHHC, (SEQ ID NO: 5)

(6) CTLNSHSNC, (SEQ ID NO: 6)

(7) CEISAKRTC, (SEQ ID NO: 7)

(8) CHILHAQAC, (SEQ ID NO: 8)

(9) CPRPPSLEC, (SEQ ID NO: 9)

(10) CTGHWASEC, (SEQ ID NO: 10)

(11) CSYEKRPMC, and (SEQ ID NO: 11)

(12) CLTKSYTSC. (SEQ ID NO: 12)

2. A method for producing from at least one species of eukaryotic cells a multipolar cell having three or more centrosomes and a multipolar spindle, the method comprising
culturing target eukaryotic cells, and
supplying the target eukaryotic cells being cultured with a synthetic peptide consisting of an amino acid sequence selected from the following amino acid sequences that act as FtsZ inhibitors or FtsA inhibitors:

(1) CSSATGKSC, (SEQ ID NO: 1)

(2) CLAPSPSKC, (SEQ ID NO: 2)

(3) CLGQTKMRC, (SEQ ID NO: 3)

(4) CGHRPYQYC, (SEQ ID NO: 4)

(5) CWAFPLHHC, (SEQ ID NO: 5)

(6) CTLNSHSNC, (SEQ ID NO: 6)

(7) CEISAKRTC, (SEQ ID NO: 7)

(8) CHILHAQAC, (SEQ ID NO: 8)

(9) CPRPPSLEC, (SEQ ID NO: 9)

(10) CTGHWASEC, (SEQ ID NO: 10)

(11) CSYEKRPMC, (SEQ ID NO: 11)
and

(12) CLTKSYTSC; (SEQ ID NO: 12)
and and
an amino acid sequence that constitutes a nucleolar localization signal (NoLS) and is selected from SEQ ID NO: 13 to SEQ ID NO: 20.

3. The multipolar cell production method according to claim 1, wherein the eukaryotic cells to be cultured are synchronized in the G2 phase or M phase and the peptide is supplied to the cultured cells that have been synchronized in the G2 phase or M phase.

4. The multipolar cell production method according to claim 1, wherein cultured tumor cells are used as the eukaryotic cells.

5. The multipolar cell production method according to claim 4, wherein the tumor cells are cells derived from a squamous cell carcinoma.

6. The multipolar cell production method according to claim 2, wherein the eukaryotic cells to be cultured are synchronized in the G2 phase or M phase and the peptide is supplied to the cultured cells that have been synchronized in the G2 phase or M phase.

7. The multipolar cell production method according to claim 2, wherein cultured tumor cells are used as the eukaryotic cells.

8. The multipolar cell production method according to claim 7, wherein the tumor cells are cells derived from a squamous cell carcinoma.

\* \* \* \* \*